(12) United States Patent
Heng

(10) Patent No.: US 8,451,450 B2
(45) Date of Patent: May 28, 2013

(54) NEAR REAL TIME OPTICAL PHASE CONJUGATION

(75) Inventor: Xin Heng, Emeryville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 442 days.

(21) Appl. No.: 12/880,543

(22) Filed: Sep. 13, 2010

(65) Prior Publication Data

US 2011/0222068 A1 Sep. 15, 2011

Related U.S. Application Data

(60) Provisional application No. 61/242,129, filed on Sep. 14, 2009.

(51) Int. Cl.
*G01B 9/021* (2006.01)

(52) U.S. Cl.
USPC .......................................... 356/457; 356/458

(58) Field of Classification Search
USPC ...................... 356/432, 447, 457, 458; 359/30
See application file for complete search history.

(56) References Cited

U.S. PATENT DOCUMENTS

| | | | |
|---|---|---|---|
| 4,648,092 A | 3/1987 | Ewbank et al. | |
| 4,715,689 A | 12/1987 | O'Meara et al. | |
| 4,720,176 A | 1/1988 | Klein et al. | |
| 4,734,911 A | 3/1988 | Bruesselbach | |
| 4,762,397 A | 8/1988 | Pepper | |
| 4,767,195 A | 8/1988 | Pepper | |
| 4,773,739 A | 9/1988 | Valley et al. | |
| 4,794,605 A | 12/1988 | Aprahamian et al. | |
| 4,928,695 A | 5/1990 | Goldman et al. | |
| 5,148,157 A | 9/1992 | Florence | |
| 5,313,726 A | 5/1994 | Yaniv et al. | |
| 5,532,868 A | 7/1996 | Gnauck et al. | |
| 5,684,565 A * | 11/1997 | Oshida et al. | 355/53 |
| 5,760,388 A | 6/1998 | Swandic | |
| 5,798,853 A | 8/1998 | Watanabe | |
| 5,920,058 A | 7/1999 | Weber et al. | |
| 5,920,588 A | 7/1999 | Watanabe | |
| 6,115,123 A | 9/2000 | Stappaerts et al. | |
| 6,175,435 B1 | 1/2001 | Watanabe | |
| 6,341,026 B1 | 1/2002 | Watanabe | |
| 6,353,753 B1 | 3/2002 | Flock et al. | |

(Continued)

OTHER PUBLICATIONS

International Search Report and Written Opinion of PCT/US2010/048725 mailed on Nov. 3, 2010, 10 pages.

(Continued)

*Primary Examiner* — Michael A Lyons
(74) *Attorney, Agent, or Firm* — Kilpatrick Townsend & Stockton LLP

(57) ABSTRACT

An optical system and associated method enable near real time optical phase conjugation. In the method, a translucent medium is illuminated by a sample illumination beam. Light scattered by the medium is directed to an electronic image sensor while a reference beam is also directed to the electronic image sensor. The scattered light and the reference beam form an interference pattern at the electronic image sensor. A digital representation of the interference pattern is recorded using the electronic image sensor, and the characteristics of a conjugate of the sample beam are computed from the numerical representation. A conjugate beam having the computed characteristics is generated using a configurable optical element and directed back to the translucent medium. The generation of the conjugate beam may be accomplished using a spatial light modulator.

34 Claims, 5 Drawing Sheets

U.S. PATENT DOCUMENTS

| | | | |
|---|---|---|---|
| 6,445,470 B1 | 9/2002 | Jenkins et al. | |
| 6,504,972 B2 | 1/2003 | Watanabe | |
| 6,626,592 B2 | 9/2003 | Watanabe | |
| 6,656,588 B1 | 12/2003 | Laine et al. | |
| 6,771,853 B2 | 8/2004 | Watanabe | |
| 6,870,974 B2 | 3/2005 | Watanabe | |
| 6,882,613 B2 * | 4/2005 | Temple | 369/103 |
| 6,905,688 B2 | 6/2005 | Rosen et al. | |
| 6,926,898 B2 | 8/2005 | Rosen et al. | |
| 6,946,134 B1 | 9/2005 | Rosen et al. | |
| 6,972,322 B2 | 12/2005 | Fleer et al. | |
| 6,987,006 B2 | 1/2006 | Fleer et al. | |
| 6,989,365 B2 | 1/2006 | Fleer et al. | |
| 6,994,857 B2 | 2/2006 | Rosen et al. | |
| 7,016,583 B2 | 3/2006 | Downie et al. | |
| 7,023,786 B2 * | 4/2006 | Itoh et al. | 369/103 |
| 7,041,478 B2 | 5/2006 | Fleer et al. | |
| 7,045,318 B2 | 5/2006 | Ballance | |
| 7,056,701 B2 | 6/2006 | Fleer et al. | |
| 7,081,354 B2 | 7/2006 | Fleer et al. | |
| 7,094,577 B2 | 8/2006 | Fleer et al. | |
| 7,119,906 B2 * | 10/2006 | Pepper et al. | 356/484 |
| 7,133,427 B2 | 11/2006 | Betin et al. | |
| 7,141,547 B2 | 11/2006 | Rosen et al. | |
| 7,184,410 B1 | 2/2007 | Frankel et al. | |
| 7,218,807 B2 | 5/2007 | Alberti et al. | |
| 7,238,667 B2 | 7/2007 | Rosen et al. | |
| 7,359,063 B2 * | 4/2008 | Jungwirth | 356/484 |
| 7,410,779 B2 | 8/2008 | Fleer et al. | |
| 7,435,410 B2 | 10/2008 | Fleer et al. | |
| 7,482,013 B2 | 1/2009 | Ballance et al. | |
| 7,507,413 B2 | 3/2009 | Rosen et al. | |
| 7,507,414 B2 | 3/2009 | Rosen et al. | |
| 7,521,424 B2 | 4/2009 | Rosen et al. | |
| 7,576,907 B1 | 8/2009 | Bartels et al. | |
| 2002/0057486 A1 | 5/2002 | Tanaka | |
| 2002/0109872 A1 | 8/2002 | Hart | |
| 2003/0039001 A1 | 2/2003 | King et al. | |
| 2005/0094230 A1 | 5/2005 | Klug et al. | |
| 2005/0168749 A1 * | 8/2005 | Ye et al. | 356/458 |
| 2005/0171439 A1 | 8/2005 | Maschke | |
| 2008/0118114 A1 | 5/2008 | Takiguchi | |
| 2008/0316571 A1 | 12/2008 | MacAulay | |
| 2009/0027747 A1 * | 1/2009 | Lee et al. | 359/15 |

OTHER PUBLICATIONS

Savage, Neil, "Digital Spatial Light Modulators", Nature Photonics, vol. 3, Mar. 2009, pp. 170-172, 3 pages.

Yaqoob, Zahid et al., "Optical Phase Conjugation for Turbidity Suppression in Biological Samples", NIH Author Manuscript PMC 2688902, Jun. 1, 2009, 16 pages.

* cited by examiner

NEAR REAL TIME OPTICAL PHASE CONJUGATION

This application claims the benefit of U.S. Provisional Application No. 61/242,129, filed on Sep. 14, 2009 and titled "Near Real Time Optical Phase Conjugation", the disclosure of which is hereby incorporated herein by reference in its entirety.

BACKGROUND OF THE INVENTION

Turbid or translucent media present special problems for optical systems. For example, a medium such as biological tissue may transmit light efficiently, but may scatter the light substantially so that it is difficult to see or image through the tissue or to direct light through the tissue to a particular target. The difficulty is not primarily due to the absorption of light by the sample, but to the scattering that interferes with conventional image formation.

While the scattering may appear random, it is actually deterministic. This determinism can be used by advanced optical techniques so that it is possible to compensate for the scattering in the turbid medium. For example, Yaqoob et al. have used a holographic recording technique produce a phase conjugate mirror, in order to image through a turbid medium. See Yaqoob et al., "Optical Phase Conjugation for Turbidity Suppression in Biological Samples", Nature Photonics 2, 110-115 (2008). In the system of Yaqoob et al., an image is projected through a turbid sample, which scatters the projected light into a lithium niobate crystal. A reference beam is also directed through the crystal, and the interference pattern or hologram generated by interference of the reference beam with the scattered light is recorded by the crystal. After a time, the reference beam is switched off, and a conjugate of the reference beam is passed through the crystal, so that a conjugate of the original scattered light is produced. The conjugate of the scattered light follows (in reverse direction) the traces of the original scattered light, passing through the turbid sample, back through the imaging optics, and to a camera where an image is recorded. The effect of the scattering is thus reversed, and it is possible to image through the turbid or translucent medium.

A disadvantage of prior systems is that the recording of the hologram may take several minutes. Especially in medical treatment applications, there is a need for faster generation of a conjugate beam, to compensate for possible motion of targets.

BRIEF SUMMARY OF THE INVENTION

In one embodiment, a method comprises illuminating a translucent medium with a sample illumination beam, and directing light scattered by the medium to an electronic image sensor. The method further comprises providing a reference light beam having known characteristics, and directing the reference light beam to the electronic image sensor, such that the reference beam and the scattered light form an interference pattern on the electronic image sensor. A numerical representation of the interference pattern is digitally recorded. From the numerical representation of the interference pattern, the characteristics of a conjugate beam are computed. The conjugate beam is a conjugate of the scattered light. The method further comprises generating a conjugate beam having the computed characteristics, and directing the conjugate beam toward the translucent medium.

The method may further comprise tagging features in the translucent medium to preferentially scatter light from the sample illumination beam. In some embodiments, generating the conjugate beam further comprises programming a configurable optical element to produce the conjugate beam when a reillumination beam having known characteristics is directed through the configurable optical element, and directing a reillumination beam having the known characteristics through the configurable optical element. The sample illumination beam, the reference beam, and the reillumination beam may be produced from the same light source. The reillumination beam may be a plane wave. The reillumination beam may be a Gaussian beam. The configurable optical element may comprise a spatial light modulator. The configurable optical element may comprise an acoustic optical deflector. The configurable optical element may comprise an electro optic modulator.

In some embodiments generating the conjugate beam further comprises programming a configurable optical element to produce the conjugate beam when a reillumination beam having known characteristics is reflected from the configurable optical element, and reflecting a reillumination beam having the known characteristics from the configurable optical element. The reillumination beam may be a plane wave. The reillumination beam may be a Gaussian beam. The configurable optical element may comprise a spatial light modulator. The configurable optical element may comprise an acoustic optical deflector. The configurable optical element may comprise an electro optic modulator.

In some embodiments, the conjugate beam is of higher power than the scattered light. The conjugate beam may be directed toward the translucent medium for a longer time than is required to generate and digitally record the numerical representation of the interference pattern. The method may further comprise turning off the sample illumination beam and the reference beam when the conjugate beam is directed toward the translucent medium. In some embodiments, the light scattered by the medium comprises light traveling in generally the same direction as the sample illumination beam. In some embodiments, the light scattered by the medium comprises light reflected from the medium. Generating the conjugate beam having the computed characteristics may include generating the conjugate beam using a single light modulating device. Generating the conjugate beam having the computed characteristics may include generating the conjugate beam using two synchronized modulation devices.

In some embodiments, the translucent medium is biological tissue, and the method further comprises tagging particular structures within the biological tissue so that the tagged structures preferentially scatter more light than is scattered by untagged surrounding tissue, and consequently are more intensely illuminated by the conjugate beam than is the untagged surrounding tissue. Tagging particular structures may comprise tagging cancer cells. The method may further comprises irradiating, via the conjugate beam, the tagged cancerous cells with doses of light radiation that are detrimental to the cells.

According to other embodiments, an optical system comprises a light source that produces a sample illumination beam directed at a translucent medium, and an electronic image sensor onto which light scattered from the translucent medium is directed. The system further comprises a reference beam having known characteristics, also directed to the electronic image sensor such that an interference pattern is formed at the electronic image sensor by interference of the scattered light with the reference beam. The system also includes a processing unit programmed to record, from the electronic image sensor, a digital representation of the interference pattern, and to compute, from the digital representation, the characteristics of a conjugate beam that is the conjugate of the scattered light. The system also includes an optical device configured to produce the conjugate beam under control of the processing unit. The electronic image sensor may comprise a charge coupled device (CCD) sensor. The electronic image sensor may comprise a complementary metal oxide semiconductor (CMOS) sensor. The computed characteristics of the conjugate beam may include amplitude information and phase information. The conjugate beam directed back to the translucent medium may be of a higher power than the scattered light. The conjugate beam may be directed back to the translucent medium for a longer time than is required to generate and record the numerical representation of the interference pattern.

In some embodiments, the light scattered by the medium comprises light traveling in generally the same direction as the sample illumination beam. The light scattered by the medium may comprise light reflected from the medium. The optical device may be a spatial light modulator, and the processing unit may be further programmed to configure the spatial light modulator to produce the conjugate beam when a reillumination beam having known characteristics is impinged on the spatial light modulator. The spatial light modulator may operate in transmission. The spatial light modulator may operate in reflection. The spatial light modulator may be a single device that modulates light in both amplitude and phase. The spatial light modulator may comprise two synchronized modulation devices. The optical device may comprise an acoustic optical deflector. The configurable optical element may comprise an electro optic modulator.

DETAILED DESCRIPTION OF THE INVENTION

Figure 1:
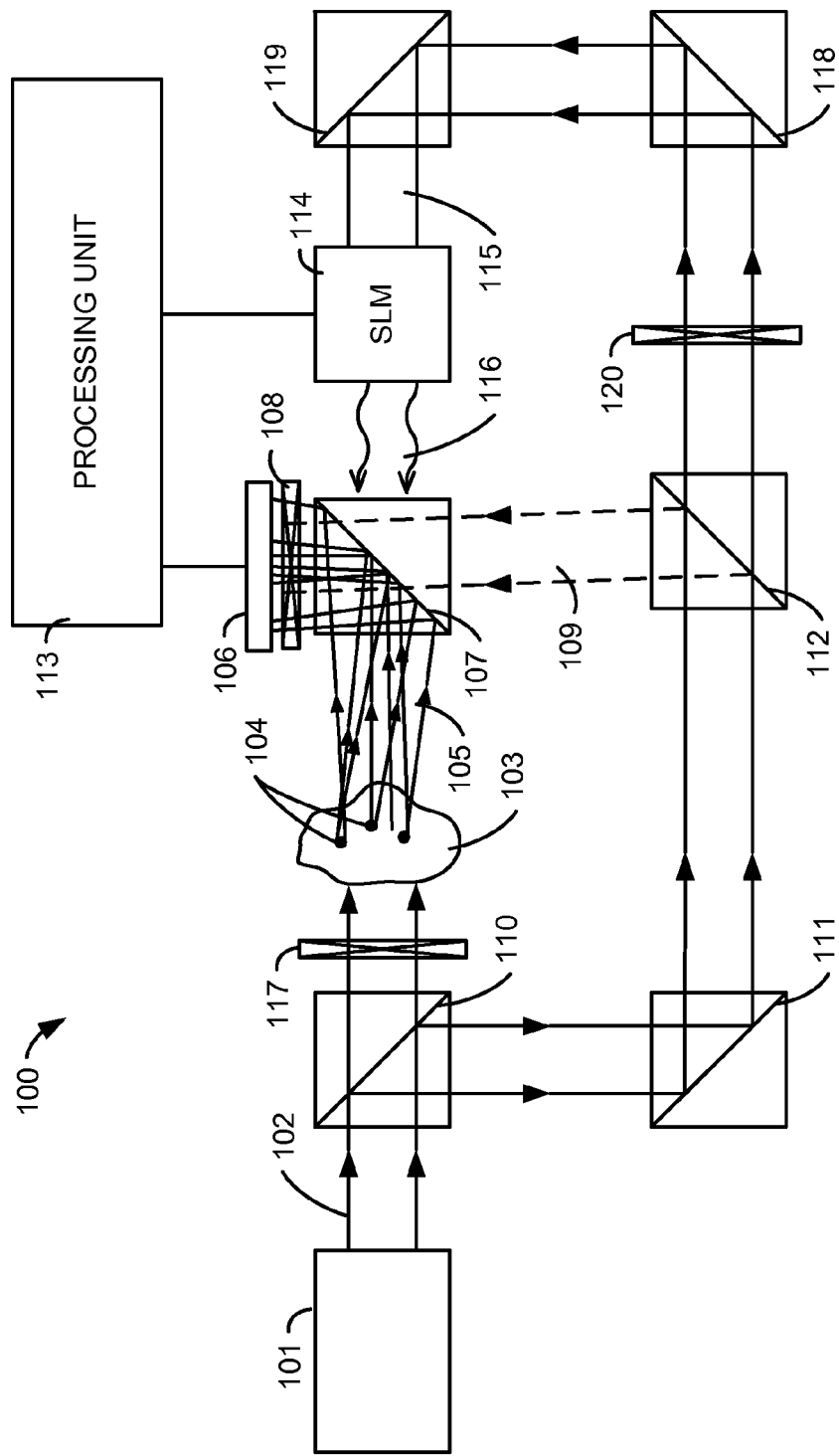
FIG. 1 illustrates an optical system in accordance with an embodiment of the invention.

FIG. 1 illustrates a system 100 in accordance with an embodiment. A laser 101 produces a sample illumination beam 102 that impinges on a turbid or translucent medium 103. Medium 103 may be, for example, a biological medium such as skin tissue, which transmits light readily, but scatters the light passing through it. Certain sites 104 within medium 103 may be tagged or labeled so that they preferentially scatter larger amounts of light than the surrounding tissue. For example, cancer cells within medium 103 may be tagged with metallic nanoparticles using known techniques.

After the sample illumination beam 102 has passed through medium 103, a sample beam 105 is produced. Sample beam 105 comprises light scattered by medium 103. The scattering appears to be random, but is in fact deterministic, and results from particular features within medium 103. Sample beam 105 is directed to an electronic image sensor 106. For example, sample beam 105 may reflect from a half-reflective mirror 107. Although not shown in FIG. 1, one or more lenses or other optical elements may be placed between medium 103 and sensor 106, for example to contain the spread of sample beam 105.

Electronic image sensor 106 preferably comprises an array of photosensitive sites that produce electric charge at a rate proportional to the intensity of light falling on them. The photosensitive sites may be called pixels. In a typical imaging operation, the charges associated with each pixel are cleared, and the pixels are exposed to light for a fixed exposure time. Those pixels receiving intense light will accumulate more electric charge than pixels receiving less intense light. After the exposure time has elapsed, the charges may be shifted into storage sites, which may be charge coupled devices. A shutter 108 may be closed to prevent further charge accumulation within sensor 106. The charges may then be shifted out of the electronic image sensor and measured, for example with the aid of a readout circuit and an analog-to-digital (A/D) converter. The resulting array of numerical values, which may be called a digital image, is a representation of the distribution of light falling on sensor 106 during the exposure time.

An electronic image sensor 106 that includes charge coupled devices may be known as a charge coupled device (CCD) sensor. Other kinds of light sensors may be used as well, for example a complementary metal oxide semiconductor (CMOS) sensor, which does not require that the charges be shifted out of the sensor for reading. A scientific CMOS (sCMOS) sensor may be used.

In system 100, a reference beam 109 is also provided to electronic image sensor 106. The characteristics of reference beam 109, for example its amplitude and phase distributions, are known. Reference beam 109 may be derived from sample illumination beam 102 by mirrors 110, 111, and 112, which provide that reference beam 109 also passes through half-reflective mirror 107 to reach sensor 106. Sample beam 105 and reference beam 109 interfere, and create an interference pattern, or hologram, at the surface of electronic image sensor 106. Sensor 106 and associated circuitry are used to digitally record a numerical representation of the interference pattern. After recording is complete, sample illumination beam 102 may be shut off from reaching medium 103, for example using a shutter 117.

A processing unit 113 is in communication with sensor 106 and receives the numerical representation of the interference pattern. Processing unit 113 may also assist in the generation of the numerical representation. For example, processing unit 113 may include an A/D converter used to digitize information from sensor 106. Processing unit 113 may be, for example, a suitably programmed computer system. Processing unit 113 computes, from the numerical representation of the interference pattern, the characteristics of a beam that is the conjugate of sample beam 105. Such a computation is well known in the art. For example, processing unit 113 may compute the amplitude and phase distributions of a beam that is the conjugate of sample beam 105.

Also provided in system 100 is a configurable optical element such as spatial light modulator 114 that can provide a beam with arbitrary amplitude and phase characteristics. Spatial light modulator 114 is but one example of a configurable optical element that can be used in embodiments of the invention. The configurable optical element could utilize an acoustic optical deflector, an electro optical modulator, or another kind of device or combination of devices. A spatial light modulator may be, for example, an array of liquid crystal devices that can modulate the amplitude and phase of a beam impinging on the device. Such devices are known in the art, and when supplied with a beam having known characteristics, can produce an approximation of a wide variety of desired beam characteristics, subject in part to the size of the liquid crystal devices. In some embodiments, spatial light modulator 114 is a single device that can modulate both amplitude and phase of a two dimensional beam shape. In other embodiments, two precisely aligned spatial light modulator devices may be used in concert, synchronized under the control of a computer and electronic circuitry, to provide amplitude and phase modulation.

Processing unit 113 is in communication with spatial light modulator 114, and configures spatial light modulator 114 to produce the conjugate beam whose characteristics were computed earlier. A reillumination beam 115, which may be a plane wave, Gaussian beam, or other suitable beam having known characteristics, is supplied to spatial light modulator 114, which modulates the wave into the desired conjugate beam 116. Reillumination beam 115 may be derived from sample illumination beam 102, for example using mirrors 118 and 119 to redirect a portion of sample illumination beam 102. A shutter 120 or other means may be provided to shut off reillumination beam 115, for example during recording of the interference pattern by sensor 106.

Figure 2:
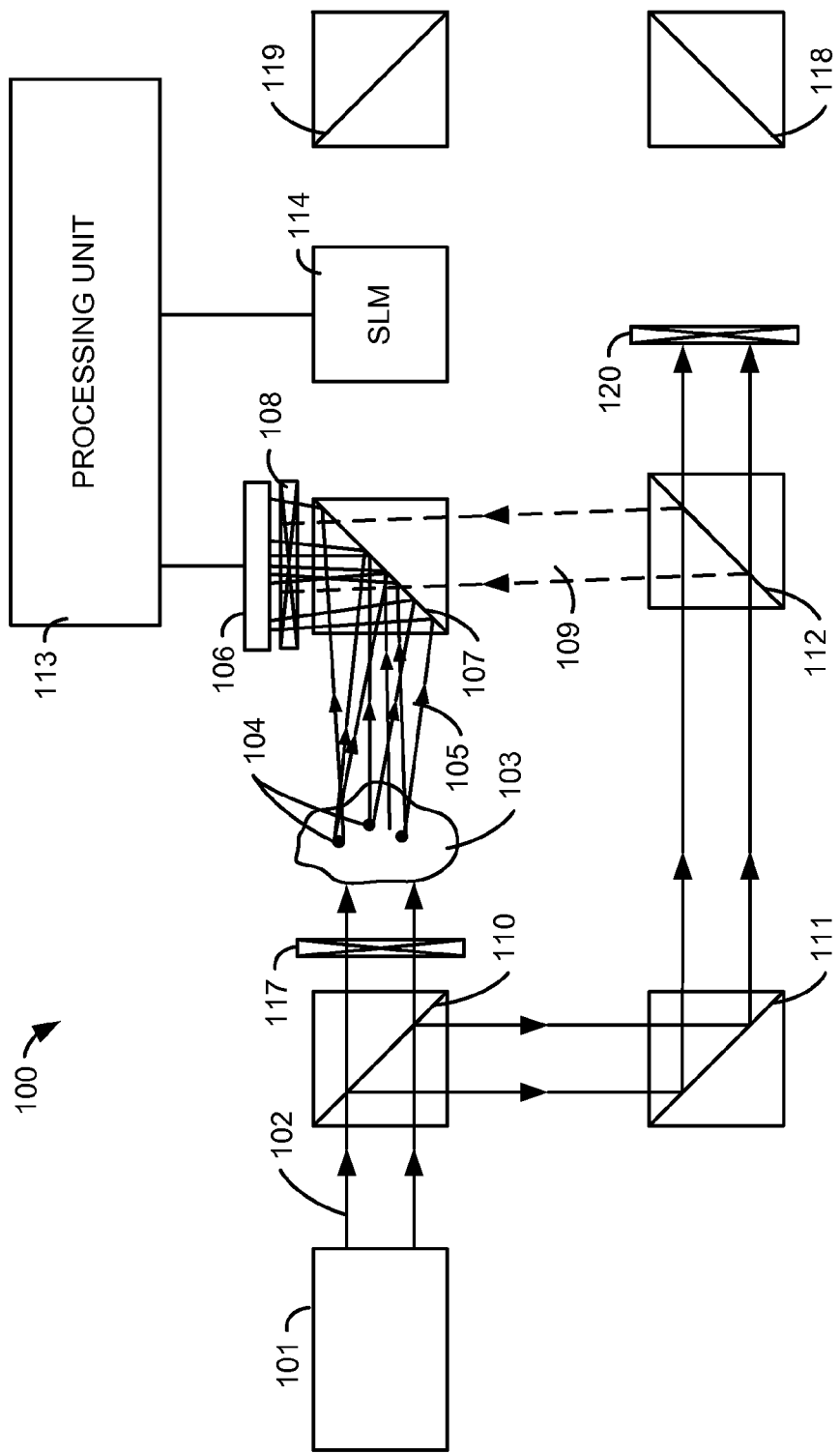
FIG. 2 illustrates the optical system of FIG. 1, configured for recording of a hologram.

FIG. 2 shows system 100 in configuration for recording of the interference pattern. In this configuration, shutter 117 is open so that sample beam 105 reaches sensor 106. Shutter 120 is closed, so that no wave reaches spatial light modulator 114.

Figure 3:
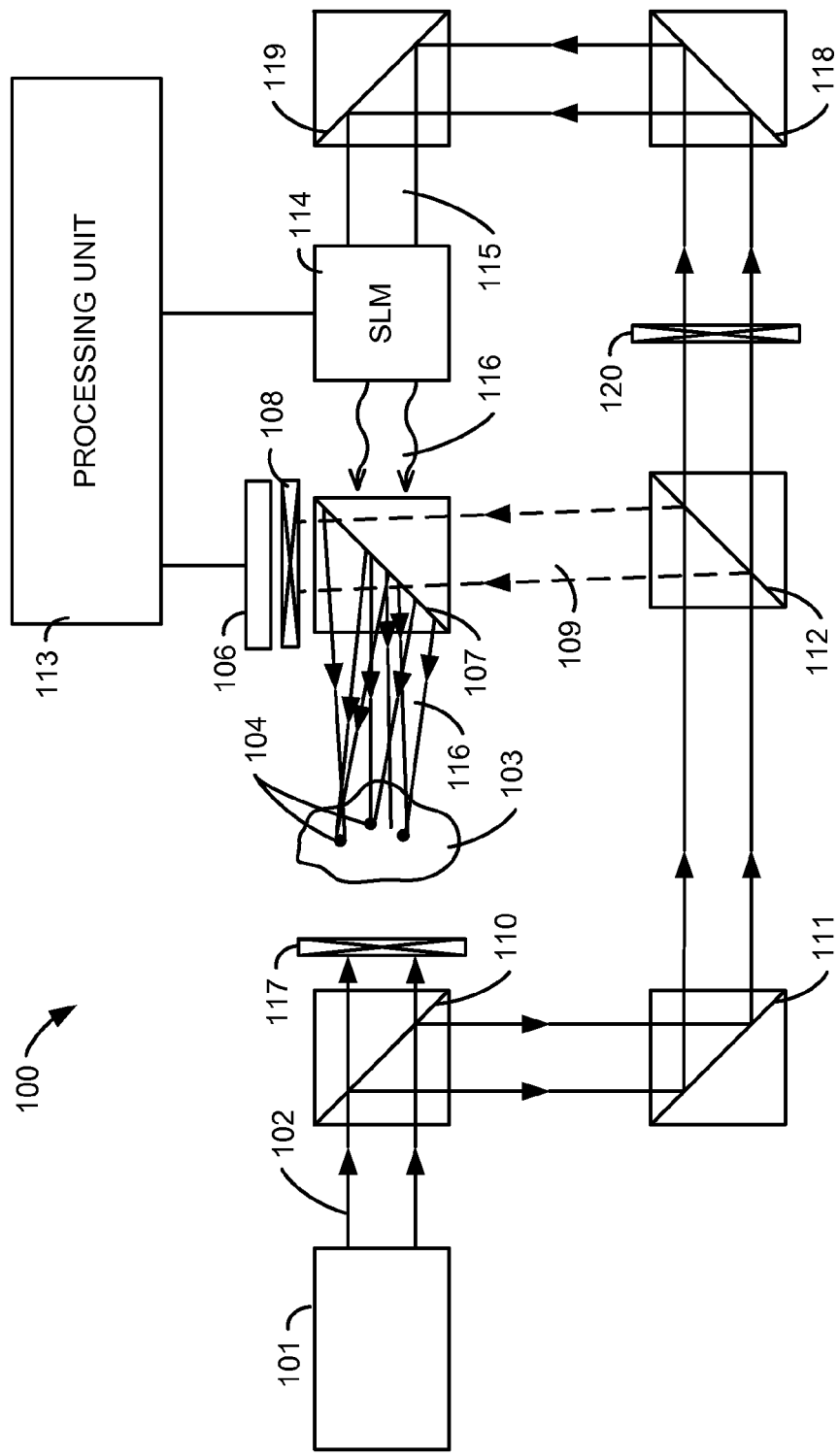
FIG. 3 illustrates the optical system of FIG. 1, configured for re-irradiating a scattering medium.

FIG. 3 shows system 100 in configuration for re-irradiation of medium 103. In this configuration, shutter 117 is closed to prevent sample illumination beam 102 from reaching medium 103 directly. Shutter 120 is open, so that reillumination beam 115 reaches spatial light modulator 114, and conjugate beam 116 is produced. Because conjugate beam 116 is a conjugate of sample beam 105, and is aligned with sample beam 105, conjugate beam 116 may be thought of as a bundle of rays that retrace, in opposite directions, the ray paths of sample beam 105. That is, light in conjugate beam 116 travels to the places and features in medium 103 from which light was scattered to create sample beam 105. This is true even if there are additional lenses or other optical elements used to shape or modify sample beam 105, so long as conjugate beam 116 also traverses the additional optical elements. The effects of such elements are present in the interference pattern read by sensor 106, and are thus compensated in conjugate beam 116.

Because the recording of the interference pattern, computation of the conjugate beam characteristics, and configuration of spatial light modulator 114 or other kind of configurable optical element can be accomplished quite quickly, for example in a fraction of a second, the system can re-irradiate medium 103 very quickly after its scattering is characterized. This near-real-time aspect of system 100 may be especially useful in medical applications. For example, medium 103 may be skin having cancerous cells tagged to preferentially scatter light from sample illumination beam 102. A possible treatment may be to preferentially irradiate the tagged cancerous cells with doses of light radiation that are detrimental to the cells, for example due to heat generation (thermolysis), protein inactivation, or acoustic wave generation, while sparing the surrounding cells due to their lower dose of light radiation. Preferably, the target cells scatter significantly more light than the surrounding cells, ideally at least 100 times more. The success of such a treatment may depend on the accurate identification of the locations of the cancerous cells, and the prompt subsequent dosing with radiation, before the cells or medium have moved. It is anticipated that this treatment technique may be effective to deliver targeted light radiation into biological tissue to a depth of 10 millimeters or more.

In one mode of operation, the light used to re-irradiate medium 103 (supplied by conjugate beam 116) is of a higher dose than the amount of light used to characterize sample beam 105. For example, once sample beam 105 is characterized, a higher laser power may be used to supply reillumination beam 115, and consequently conjugate beam 116, so that conjugate beam 116 is of a much higher power than sample beam 105. In this way, the tagged cells may be preferentially given a large dose of light illumination before medium 103 can move. In another mode of operation, conjugate beam 116 may simply be supplied for a longer time than was required for generating and recording the numerical representation of the interference pattern. In other modes or applications, conjugate beam 116 need not be of higher power than sample beam 105, or supplied for a longer time than was required for generating and recording the numerical representation of the interference pattern.

If moderate motion of medium 103 or particular cells within it is expected, system 100 may be used in a cyclic manner. For example if it is expected that the target cells may move such that a characterization of their locations will only be sufficiently accurate for one second, then medium 103 may be characterized, and then re-irradiated for a period of time less than one second. At that time, medium 103 may be re-characterized, and another period of re-irradiation provided. The cycle may be repeated if necessary, and may recur at any suitable interval, which may be shorter or longer than one second in other example embodiments. The maximum speed of repetition is governed by how fast the conjugate beam can be computed and generated. The accuracy of delivery of light to the targeted locations in medium 103 is governed in part by the quality of the optical elements used, the pixel size of the digital image sensor, and the characteristics of the spatial light modulator.

The operation of system 100 may be described mathematically as follows. The scattering characteristics of medium 103 may be represented by a scattering matrix $$\begin{bmatrix} S_{11} & S_{12} \\ S_{21} & S_{22} \end{bmatrix}.$$

If sample illumination beam 102 is described by $$\begin{bmatrix} a_1 \\ 0 \end{bmatrix}$$

(because incidence on the sample is from only one side), then sample beam 105, after being scattered by medium 103, is described by $$\begin{bmatrix} b_1 \\ b_2 \end{bmatrix} = \begin{bmatrix} S_{11} & S_{12} \\ S_{21} & S_{22} \end{bmatrix} \begin{bmatrix} a_1 \\ 0 \end{bmatrix}.$$

After recording, the processing unit will have information about the interference of $b_2 = S_{21} a_1$ and the known reference beam. After computing the characteristics of conjugate beam 116, the processing unit has information about the kind of beam that the spatial light modulator should produce, which can be represented as $S_{21}^{*}a_{1}^{*}$. The values in this expression are all complex, indicating that the sample beam is characterized in both amplitude and phase. Conjugate beam 116 will once again be "scattered" by medium 103, so that the resulting beam can be represented as $H=S_{12}CS_{21}^{*}a_{1}^{*}$, where C is a factor to account for absorption in medium 103 and other losses in the system. Assuming C is a scalar, and because $S_{12}=S_{21}, \rightarrow H \approx Ca_{1}^{*}$, indicating that conjugate beam 116 essentially retraces sample beam 105.

Figure 4:
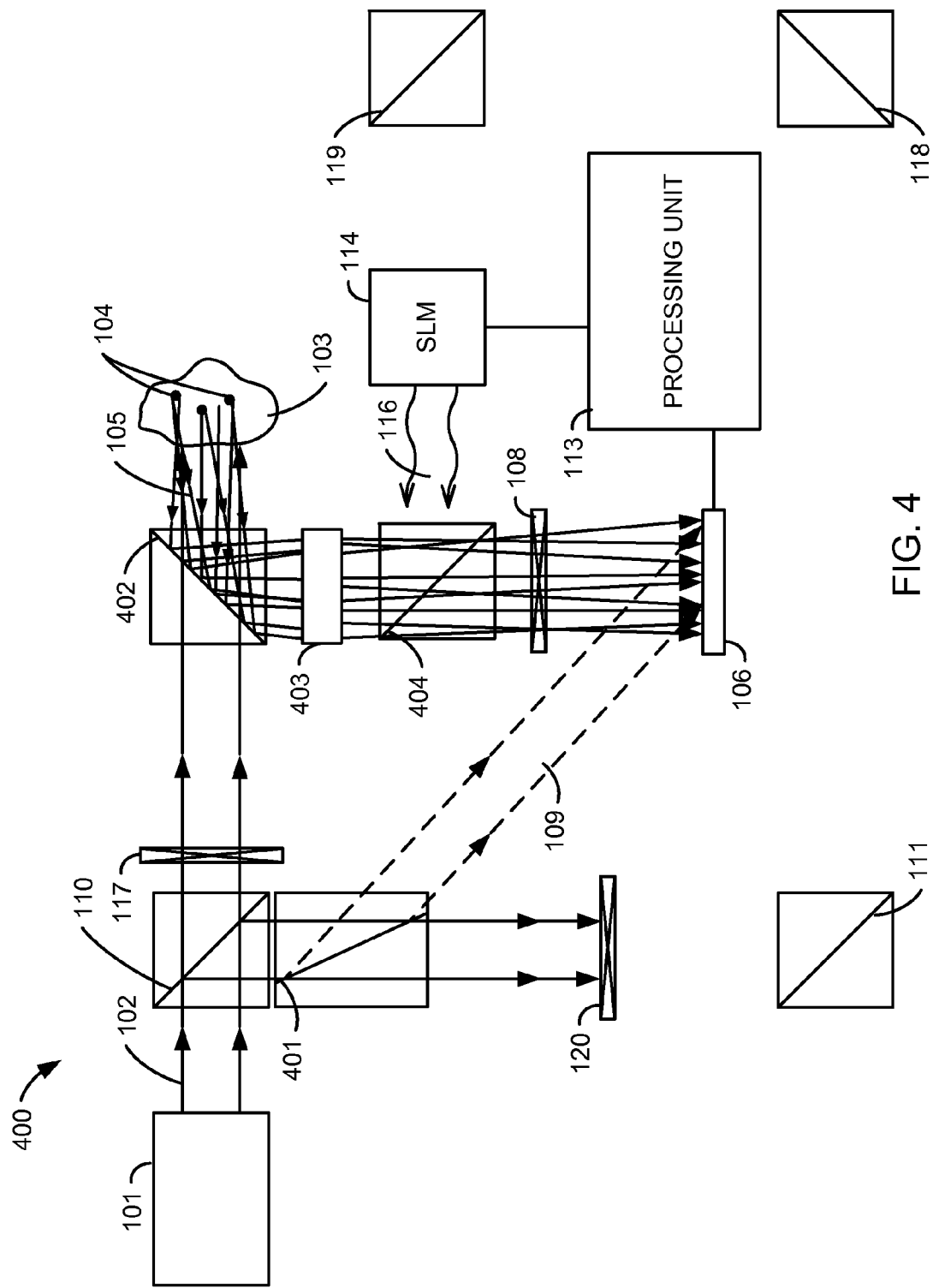
FIG. 4 illustrates an optical system in accordance with another example embodiment, configured for recording of an interference pattern.

In another embodiment, the system may be operated in a reflection mode. In the embodiments described above, sample beam 105 continues through medium 103 after scattering from sites 104, traveling generally in the same direction as illumination beam 102. In those embodiments, the sample beam comprised light resulting from forward scattering. FIG. 4 shows an example alternate system 400, in which sample beam 105 comprises light reflected from sites 104 and traveling generally in the opposite direction of illumination beam 102. In this embodiment, sample beam 105 comprises light resulting from back scatter. Systems using other reflected light, for example side scatter, may be envisioned. FIG. 4 shows system 400 configured for recording of an interference pattern at sensor 106. In this arrangement, shutters 117 and 108 are open, and shutter 120 is closed.

Sample illumination beam 102 passes through partially reflective mirror 110. A portion of sample illumination beam 102 encounters a second partially reflective mirror 401, which diverts some of the light impinging on it to form reference beam 109, aimed at sensor 106. Another portion of sample illumination beam 102 passes through mirror 110 and encounters another partially reflective beam splitting mirror 402. Mirror 402 may reflect more light than it transmits. For example, mirror 402 may reflect approximately 80 to 90 percent of the light impinging on it, and reflect approximately 10 to 20 percent. (A small amount of light may also be absorbed.) Other ratios of transmission to reflection could be used. For example, mirror 402 may be nominally half reflective. The transmitted portion of sample illumination beam continues to medium 103, where some of it is reflected to form sample beam 105. Particular sites 104 within medium 103 may preferentially reflect light, as compared with other parts of medium 103.

Sample beam 105 again encounters partially reflective mirror 402, and a portion of sample beam 105 is reflected. Sample beam 105 may optionally pass through imaging optics 403, which may constrain the divergence of sample beam 105. Sample beam 105 then encounters another partially reflective mirror 404. Mirror 404 may transmit more light than it reflects. For example, mirror 404 may transmit approximately 80 to 90 percent of the light impinging on it, and reflect approximately 10 to 20 percent. Other ratios of transmission to reflection could be used. For example, mirror 404 may be nominally half reflective. The portion of sample beam 105 transmitted by mirror 404 passes through open shutter 108 and reaches electronic sensor 106. An interference pattern is formed at sensor 106 by the interference of reference beam 109 with the portion of sample beam 105 reaching sensor 106. Sensor 106 and associated circuitry are used to digitally record a numerical representation of the interference pattern. After recording is complete, sample illumination beam 102 may be shut off from reaching medium 103, for example using a shutter 117. Processing unit 113 receives the numerical representation of the interference pattern, and computes the characteristics of a conjugate beam. For example, processing unit 113 may compute the amplitude and phase distributions of a beam that is the conjugate of sample beam 105, as received by sensor 106.

Figure 5:
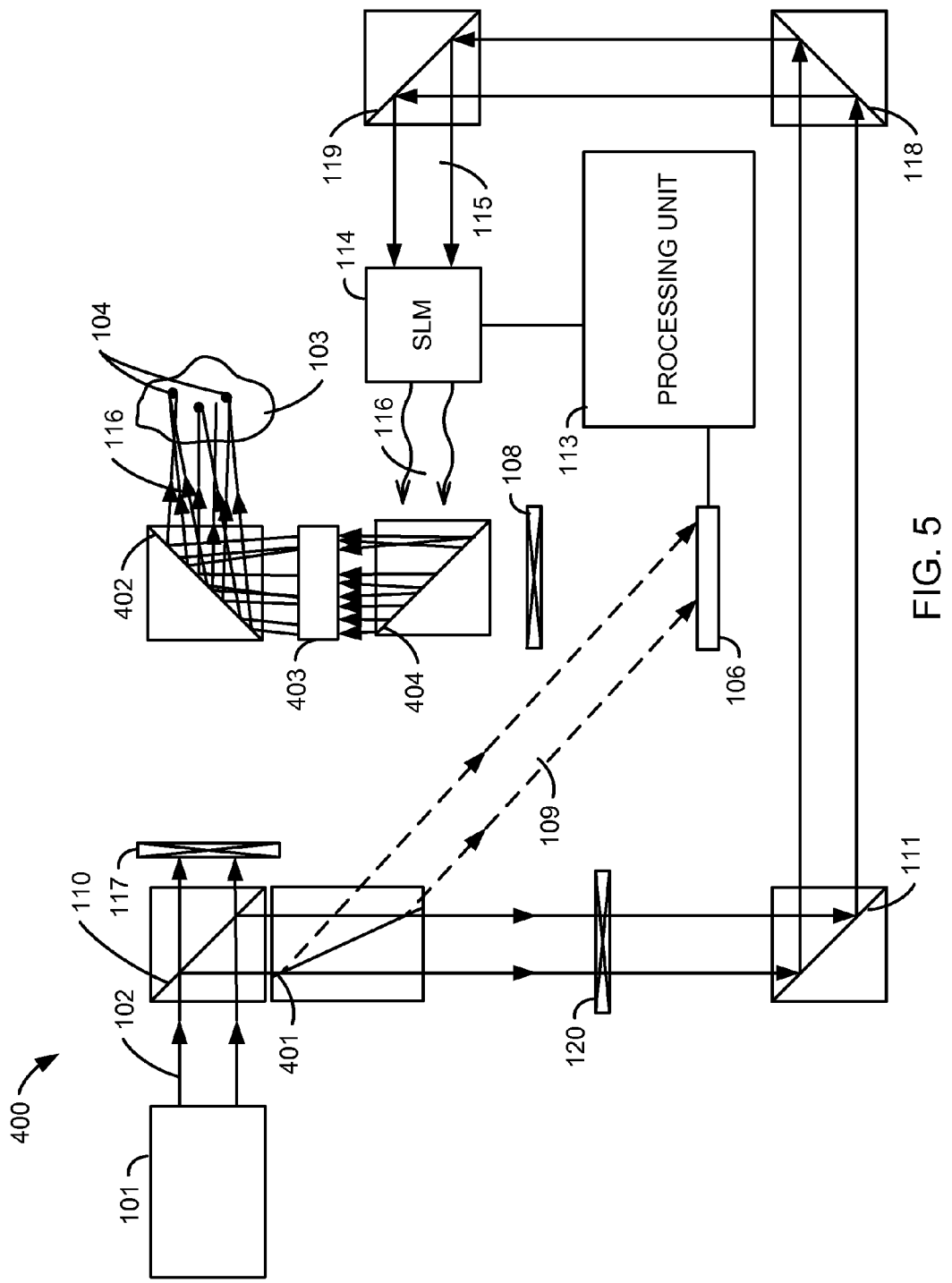
FIG. 5 illustrates the optical system of FIG. 4, in configuration to re-irradiate a medium.

FIG. 5 shows system 400 in configuration to re-irradiate medium 103. In this configuration, shutter 117 is closed to prevent sample illumination beam 102 from reaching medium 103 directly. Processing unit 113 is in communication with spatial light modulator 114, and configures spatial light modulator 114 or other configurable optical device to produce the conjugate beam whose characteristics were computed earlier. A reillumination beam 115, which may be a plane wave, Gaussian beam, or other suitable beam, is supplied to spatial light modulator 114, which modulates the wave into the desired conjugate beam 116. Reillumination beam 115 may be derived from sample illumination beam 102, for example using mirrors 111, 118 and 119 to redirect a portion of sample illumination beam 102. Shutter 108 is preferably closed, to block any of reference beam 109 reflected from sensor 106.

As before, conjugate beam 116 retraces sample beam 105, thus re-irradiating the portions of medium 103 that reflected light from sample illumination beam 102. Conjugate beam 116 may be or higher, equal, or lower power than sample beam 105. In some embodiments, conjugate beam 116 may be supplied for a longer time than was required for generating and recording the numerical representation of the interference pattern.

The embodiments described above include a spatial light modulator 114 that operates in transmission, modulating light passing through spatial light modulator 114. One of skill in the art will recognize that the optical arrangement may be easily reconfigured for use of a spatial light modulator that operates by reflection, modulating light reflecting from the spatial light modulator. Reflection-mode spatial light modulators are available from Cambridge Research and Instrumentation, of Woburn, Mass., USA. A reflection-mode spatial light modulator is also described in U.S. Pat. No. 7,576,907 to Bartels et al., which patent is hereby incorporated by reference herein for all purposes.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A method, comprising:
   illuminating a translucent medium with a sample illumination beam;
   directing light scattered by the medium to an electronic image sensor;
   providing a reference light beam having known characteristics;
   directing the reference light beam to the electronic image sensor, such that the reference beam and the scattered light form an interference pattern on the electronic image sensor;
   digitally recording a numerical representation of the interference pattern;
   computing, from the numerical representation of the interference pattern, the characteristics of a conjugate beam, the conjugate beam being a conjugate of the scattered light;
   generating a conjugate beam having the computed characteristics; and directing the conjugate beam toward the translucent medium.

2. The method of claim 1, further comprising tagging features in the translucent medium to preferentially scatter light from the sample illumination beam.

3. The method of claim 1, wherein generating the conjugate beam further comprises:
programming a configurable optical element to produce the conjugate beam when a reillumination beam having known characteristics is directed through the configurable optical element; and
directing a reillumination beam having the known characteristics through the configurable optical element.

4. The method of claim 3, wherein the sample illumination beam, the reference beam, and the reillumination beam are produced from the same light source.

5. The method of claim 3, wherein the reillumination beam is a plane wave or a Gaussian beam.

6. The method of claim 3, wherein the configurable optical element comprises a spatial light modulator.

7. The method of claim 3, wherein the configurable optical element comprises at least one device selected from the group consisting of an acoustic optical deflector and an electro optical modulator.

8. The method of claim 1, wherein generating the conjugate beam further comprises:
programming a configurable optical element to produce the conjugate beam when a reillumination beam having known characteristics is reflected from the configurable optical element; and
reflecting a reillumination beam having the known characteristics from the configurable optical element.

9. The method of claim 8, wherein the reillumination beam is a plane wave or a Gaussian beam.

10. The method of claim 8, wherein the configurable optical element comprises a spatial light modulator.

11. The method of claim 8, wherein the configurable optical element comprises at least one device selected from the group consisting of an acoustic optical deflector and an electro optical modulator.

12. The method of claim 1, wherein the conjugate beam is of higher power than the scattered light.

13. The method of claim 1, wherein the conjugate beam is directed toward the translucent medium for a longer time than is required to generate and digitally record the numerical representation of the interference pattern.

14. The method of claim 1, further comprising turning off the sample illumination beam and the reference beam when the conjugate beam is directed toward the translucent medium.

15. The method of claim 1, wherein the light scattered by the medium comprises light traveling in generally the same direction as the sample illumination beam.

16. The method of claim 1, wherein the light scattered by the medium comprises light reflected from the medium.

17. The method of claim 1, wherein generating the conjugate beam having the computed characteristics comprises generating the conjugate beam using a single light modulating device.

18. The method of claim 1, wherein generating the conjugate beam having the computed characteristics comprises generating the conjugate beam using two synchronized modulation devices.

19. The method of claim 1, wherein the translucent medium is biological tissue, the method further comprising:
tagging particular structures within the biological tissue so that the tagged structures preferentially scatter more light than is scattered by untagged surrounding tissue, and consequently are more intensely illuminated by the conjugate beam than is the untagged surrounding tissue.

20. The method of claim 19, wherein tagging particular structures comprises tagging cancer cells.

21. The method of claim 20, further comprising irradiating, via the conjugate beam, the tagged cancerous cells with doses of light radiation that are detrimental to the cells.

22. An optical system, comprising:
a light source that produces a sample illumination beam directed at a translucent medium;
an electronic image sensor onto which light scattered from the translucent medium is directed;
a reference beam having known characteristics, also directed to the electronic image sensor such that an interference pattern is formed at the electronic image sensor by interference of the scattered light with the reference beam;
a processing unit programmed to record, from the electronic image sensor, a digital representation of the interference pattern, and to compute, from the digital representation, the characteristics of a conjugate beam that is the conjugate of the scattered light;
an optical device configured to produce the conjugate beam under control of the processing unit.

23. The optical system of claim 22, wherein the electronic image sensor comprises a charge coupled device (CCD) sensor or a complementary metal oxide semiconductor (CMOS) sensor.

24. The optical system of claim 22, wherein the computed characteristics of the conjugate beam include amplitude information and phase information.

25. The optical system of claim 22, wherein the conjugate beam directed back to the translucent medium is of a higher power than the scattered light.

26. The optical system of claim 22, wherein the conjugate beam is directed back to the translucent medium for a longer time than is required to generate and record the numerical representation of the interference pattern.

27. The optical system of claim 22, wherein the light scattered by the medium comprises light traveling in generally the same direction as the sample illumination beam.

28. The optical system of claim 22, wherein the light scattered by the medium comprises light reflected from the medium.

29. The optical system of claim 22, wherein the optical device comprises a spatial light modulator, and wherein the processing unit is further programmed to configure the spatial light modulator to produce the conjugate beam when a reillumination beam having known characteristics is impinged on the spatial light modulator.

30. The optical system of claim 29, wherein the spatial light modulator operates in transmission.

31. The optical system of claim 29, wherein the spatial light modulator operates in reflection.

32. The optical system of claim 29, wherein the spatial light modulator is a single device that modulates light in both amplitude and phase.

33. The optical system of claim 29, wherein the spatial light modulator comprises two synchronized modulation devices.

34. The optical system of claim 22, wherein the optical device comprises at least one device selected from the group consisting of an acoustic optical deflector and an electro optical modulator.

* * * * *